United States Patent [19]

Blumbergs et al.

[11] Patent Number: 4,617,394

[45] Date of Patent: Oct. 14, 1986

[54] 4-METHYL-5-(UNSUBSTITUTED AND SUBSTITUTED PHENOXY)-2,6-DIMETHOXY-8-(AMINOALKYLAMINO) QUINOLINES

[75] Inventors: Peter Blumbergs, Royal Oak, Mich.; Maurice P. LaMontagne, Overland Park, Kans.

[73] Assignee: The United States of America as represented by the Secretary of the Army, Washington, D.C.

[21] Appl. No.: 787,143

[22] Filed: Oct. 15, 1985

[51] Int. Cl.$^4$ .................... C07D 215/22; A61K 31/47
[52] U.S. Cl. ..................................... 546/157; 546/153
[58] Field of Search ........................................ 546/157

[56] References Cited

U.S. PATENT DOCUMENTS 4,431,807  2/1984  Struve ................................. 546/171

OTHER PUBLICATIONS

Mislow, Journal of the American Chemical Society, vol. 68, pp. 1553–1556, (1946).

Chen, Journal of Medicinal Chemistry, vol. 20, pp. 1107–1109, (1977).

Primary Examiner—Donald G. Daus
Assistant Examiner—Robert Benson
Attorney, Agent, or Firm—Ian C. McLeod

[57] ABSTRACT

Compounds of the class including 4-methyl-5-(unsubstituted and substituted phenoxy)-2,6-dimethoxy-8-(aminoalkylamino)quinolines as the free bases and pharmaceutically acceptable acid amine salts are described. The compounds are highly effective antimalarial agents which possess both tissue schizonticidal (radical curative) and blood schizonticidal (suppressive) acitivity. In addition, these drugs have significantly better therapeutic indices than primaquine which is the current tissue schizonticidal drug of choice. Primaquine possesses no useful blood schizonticidal activity at tolerated dose levels. The new 2-methoxy substituted compounds produce markedly less methemoglobin at effective dose levels and thus permit a higher degree of safety than analogs which are unsubstituted in the 2-position.

5 Claims, No Drawings

4-METHYL-5-(UNSUBSTITUTED AND SUBSTITUTED PHENOXY)-2,6-DIMETHOXY-8-(AMINOALKYLAMINO) QUINOLINES

DESCRIPTION OF THE INVENTION

1. Field of the Invention

The present invention relates to compounds of the class including 4-methyl-5-(unsubstituted and substituted phenoxy)-2,6-dimethoxy-8-(aminoalkylamino)-quinolines which are useful as antimalarials in mammals. A substituted phenoxy group which is 3-trifluoromethylphenoxy is preferred.

2. Prior Art

The class of compounds with which the present invention is concerned generally includes primaquine, 8-(4-amino-1-methylbutylamino)-6-methoxyquinoline, which has the formula:

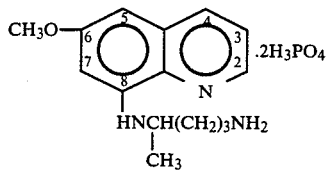

Primaquine, over the years, has been the clinical drug of choice with widespread use in the treatment of relapsing *Plasmodium vivax* and *P. ovale* malaria. Primaquine, used clinically as the diphosphate salt, is a causal prophylactic and radical curative drug which is effective in clearing the tissues of parasites, but it has only very minimal suppressive activity, i.e., it is relatively ineffective as a blood schizonticide. In man, the toxicity of primaquine precludes administration of a single curative dose. Thus to achieve a radical cure of *P. vivax* in man, the dose is ordinarily given in divided doses over 14 to 21 days. This is accompanied with a three-day course of chloroquine, a suppressive drug to clear the blood of schizonts which may "leak" from the tissue cycle of parasite development.

As part of early attempts to improve primaquine, the side chain attached to the 8-position of the quinoline nucleus was variously modified as part of the extensive Army World War II Program, but no significant improvement was achieved.

Later in 1955, Elderfield and co-workers, *Journal of the American Chemical Society*, 77, 4816 (1955), reported the synthesis of 4-methylprimaquine which, more recently, has been tested in modern and well-developed test systems and represents a compound in the prior art with radical curative activity slightly more effective than primaquine. The results for 4-methylprimaquine, relative to primaquine, are shown in Table I for both radical curative and suppressive activity.

TABLE 1

Comparison of the Antimalarial Activity of the Better Prior Art Radical Curative Drugs with Primaquine

| Compound | Suppressive Activity *P. Berghei*, Rane Mouse Test Dose, mg/kg ΔMST, Days; 5 mice | | | | | Radical Curative Activity *P. cynomolgi*, Seato Rhesus Dose, mg/kg (× 7) | | | |
|---|---|---|---|---|---|---|---|---|---|
| | 40 | 80 | 160 | 320 | 640 | 3.16 | 1.3 | 1.0 | 0.316 |
| Primaquine Diphosphate | I | I | 9(A) | 2/5T | 5T | | 6/6C | 1/2C | 0/2C |
| 4-Methyl-primaquine diphosphate | I | I | 9(A) | 10(A) | 3C,1T | | | 2/2C | 0/4C |
| 5-(4-Fluorophenoxy) primaquine citrate | I | 7.0(A) | 9(A) | 5C | 5C | 1/1C | | 1/3C | 0/2C |

I = Inactive,
A = Active, increase in survival time of 7 days or more relative to controls;
T = Toxic Death,
C = Cures.

The data indicate that 4-methylprimaquine, as a radical curative drug, is comparable to primaquine and somewhat greater in potentcy. Thus, 4-methylprimaquine gives 100% cures at 1.0 mg/kg, whereas primaquine gives 100% cures at 1.3 mg/kg and 50% cures at 1.0 mg/kg (½ cures). Both are inactive at 0.316 mg/kg. In the suppressive test, both display very weak activity at non-toxic dose levels, and 4-methylprimaquine is curative only at the toxic dose of 640 mg/kg. Subsequent modifications in the 4-position, M. P. LaMontagne, et al, *Journal of Medicinal Chemistry*, 20, 1122 (1977), failed to yield a more effective analog.

Concurrently E. M. Chen, et al *Journal of Medicinal Chemistry*, 20, 1107 (1977) reported the preparation of a series of 5-substituted analogs of primaquine. Of the series of compounds reported in the cited reference, the most active representative was 5-(4-fluorophenoxy)-primaquine, the results for which are shown also in Table 1. The compound is no more active than primaquine in the Rhesus model as a radical curative drug. As a suppressive drug, it is active (and non-toxic) in mice at the high dose levels of 320 and 640 mg/kg. While this is a slight improvement relative to primaquine, it is distinctly inferior to newly developed clinical suppressive drugs such as mefloquine which is curative in the Rane Mouse Test at dose levels as low as 20 mg/kg. Accordingly, 5-(4-fluorophenoxy)primaquine is not an effective suppressive drug and its radical curative activity is not significantly better than that of primaquine.

The oxidation of hemoglobin to methemoglobin is known to be caused in mammals by various chemical agents and the pathological consequence is called methemoglobinemia. Methemoglobin does not transport oxygen to the tissues. The physical performance of the animal is restricted because of the lack of oxygen and this condition may be life threatening. After use of the methemoglobin-producing drug is stopped, the blood will return to normal. If the methemoglobinemia goes past a certain level, death results from anoxia. Thus increased levels of methemoglobin are very undesirable as a side effect of the treatment of most diseases in mammals. Antimalaria drugs such as primaquine and substituted primaquines cause methemoglobinemia to an extent dependent on their structure.

U.S. Pat. No. 4,431,807 to Strube and LaMontagne describes analog compounds which are 4-methyl-5-(unsubstituted or substituted phenoxy) 6-methoxy-8-(aminoalkyl amino)quinolines and which are unsubstituted in the 2-position. These compounds are much improved over the prior art compounds shown in Table I at low dosages in both suppressive and radical curative tests. However, it has been found that these compounds induce methemoglobin formation in animals which, as just discussed, can be of consequence in the treatment of mammals including humans.

OBJECTS OF THE INVENTION

It is therefore an object of this invention to provide a novel series of primaquine analog compounds which are also analogs of those described in U.S. Pat. No. 4,431,807, which are unexpectedly active as antimalarial agents at very low dose levels, which are unexpectedly effective against both tissue and blood schizonts and which, importantly, have a limited affect on methemoglobin formation. The high activity is unexpected in view of the fact that other related 2-position substituents have resulted in compounds with reduced antimalarial activity and increased toxicity.

GENERAL DESCRIPTION OF THE INVENTION

The present invention relates to compounds of the formula:

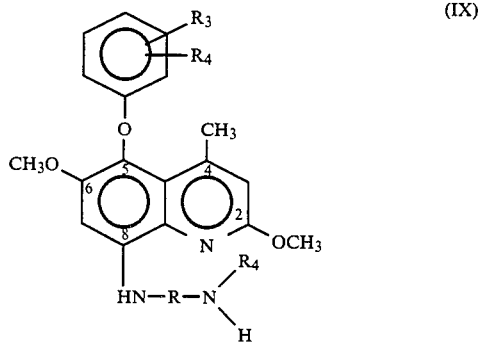

(IX)

wherein R is an alkylene group which is

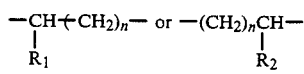

wherein n is 3 or 4, wherein $R_1$ and $R_2$ are methyl or ethyl, wherein $R_3$ and $R_4$ are hydrogen, chloro, bromo, fluoro, trifluoromethyl or methoxy groups, and wherein the compound is a free amine or a pharmaceutically acceptable acid amine salt.

The preferred compound within this class is 8-(4-amino-1-methylbutylamino)-2,6-dimethoxy-4-methyl-5-(3-trifluoromethylphenoxy)quinoline (Compound IX).

The pattern of worth for representatives of Structure IX such as the succinate amine salt (X) have been established through the use of highly standardized tests in experimental animals. The preferred mode for administering these compounds consists in the use of non-toxic acid-addition salts, inclusive of those formed from Structure IX and acids such as hydrochloric, hydrobromic, succinic, sulfamic, sulfuric, phosphoric, citric, tartaric, methanesulfonic, isethionic, aceturic, malic, fumaric, beta-resorcyclic, or pamoic acid. Said salts may be administered orally in the form of tablets, capsules, or dragees when admixed with solid excipients such as lactose, sucrose, starch, microcrystalline cellulose, magnesium stearate or talc. The foregoing compositions are preferred means for oral administration over the use of flavored syrups or tinctures containing the antimalarial drug. Under special circumstances, parenteral administration may be indicated, employing an aqueous solution or an oleaginous formulation of the agent. Aqueous solutions can be prepared in water, physiological saline, Ringer's solution, or the like, either with or without buffers. Oleaginous formulations may be made in natural oils (as, peanut oil or olive oil), or in benzyl benzoate, for example. The several possible isomeric forms of Structure X are to be included among the preferred antimalarials, and advantage may accrue in the choice of one or other of these.

The compounds as the acid amine salts are more water-soluble than the free amines and are more efficiently utilized in infected animals. The preferred salts include phosphate, citrate and succinate. As salts, the compounds may be hydrated.

ANTIMALARIAL TESTING PROCEDURES IN ANIMALS

Test Protocols

The two principal testing systems used in this work to evaluate efficacy of candidate drugs are described below.

Radical Curative Test in Rhesus Monkeys, SEATO Medical Research Laboratory, Bangkok, John Brown/Richard Andre This test is designed to evaluate the tissue schizonticidal (radical curative) activity of test compounds. Well-conditioned Indian rhesus monkeys of either sex weighing 2-4 Kg are utilized. *Plasmodium cynomolgi* (strain B) sporozoites are prepared by grinding heavily infected *Anopheles dirus* salivary glands in 1:1 monkey serum-saline vehicle.

Monkeys are infected by I.V. injection of $10^6$ freshly isolated *P. cynomolgi* sporozoites on day 0. A rapidly rising parasitemia develops after a 7 to 9 day prepatient period, and administration of the test drug is initiated when the rising parasite count exceeds 5000 per $mm^3$ (typically day 10-12). Test drugs are administered orally (by nasogastric intubation) once daily for 7 consecutive days in aqueous solution or, if insoluble, in suspension in 0.3% methylcellulose solution. Chloroquine diphosphate (3.1 mg of base/kg orally per day) is always administered concurrently with the test drug for 7 days to eliminate blood schizonts. Thus any tissue schizonticidal activity of the test drug will always be apparent even if it lacks blood schizonticidal activity.

A vehicle control monkey and a positive drug control (primaquine) monkey are included in each group of inoculated monkeys.

Interpretation

The effect of the test drug is determined by counting blood parasites. Parasite counts are made daily through day 20, and every two days thereafter. Initially a clearance of blood parasites is observed due to the blood schizonticidal action of chloroquine. If exoerythrocytic parasites ("tissue schizonts") survive the action of the test drug (i.e. if the drug is inactive or incompletely active) there will be a "relapse" of blood parasites. If there is no relapse within 20 days of the initial clearance of parasitemia, the monkey is splenectomized and its parasitemia followed for an additional 30 days. If there is no relapse within this period, the experiment is terminated and the monkey is considered "cured". Alternately, in some experiments, negative parasitemia was followed for 100 days without prior splenectomy. It has been determined that the splenectomy and non-splenectomy methods yield virtually identical results.

Primaquine diphosphate cures over 90% of monkeys in this test system when administered at a dose of 1.3 mg/kg of salt per day for 7 days (1.0 mg/kg free base) in combination with chloroquine.

References

1. Schmidt, L. N., Rossan, R. N., Fradkin, R., Woods, J. Studies on the Antimalarial Activity of 1,2-Dimethoxy-4-(bis-diethylaminoethyl)-amino-5-bromobenzene. Bull. Wld. Health Organ. 34: 783-788, 1966.

2. WHO report of Procedures for Screening Potential Antimalarial Compounds held Oct. 26-29, 1971, WHO/MAL/72.763.

Blood Schizonticidal Test (Mouse), University of Miami, Rane (suppressive)

This system is based on comparisons of responses to test compounds by *Plasmodium berghei* KBG 173 malaria in mice as expressed in mean survival times and the mean survival times of untreated controls. Thus, compounds noted as active produce increases in the survival times of the treated animals that are significant when compared with the survival times of untreated controls. Since an established disease is less sensitive to treatment than a disease in the early stages of development, treatment is withheld until the parasitemia is relatively high in order to insure a more reliable assay of activity and the selection of appropriate compounds for intensive preclinical studies.

Utilizing young ICR/HA Swiss mice and a standard inoculum of *Plasmodium berghei* KBG 173, it is possible to produce a uniform disease fatal to 100% of untreated animals within 6 to 8 days with a mean survival time of 6.2 days. Test animals weigh from 18 to 22 grams but weight variations in any given experimental or control group are confined to 2 to 3 grams. All animals in any given test are approximately of the same age. Animals on test are housed in metal-topped plastic cages, given a standard laboratory diet and water ad libitum.

Test animals receive an intraperitoneal injection of 0.5 ml of 1:100 dilution of heparinized heart's blood with a minimum of 90% parasitized cells ($4 \times 10^7$ cells), drawn from donor mice infected one week earlier with *Plasmodium berghei*. The donor strain is maintained by weekly passages in separate groups of mice inoculated with a 0.5 ml of 1:500 dilution of heparinized heart's blood.

Test compounds are administered after dissolution or suspension in peanut oil. A single dose is given subcutaneously 72 hours after the mice are infected with *Plasmodium berghei*. At this time a 10-15 percent parasitemia has developed; the disease is well established but has not produced sufficient debility to alter the response of the host to toxic effects of the drug on test. Since treatment is withheld for three days to permit the infection to become well established and death occurs in untreated controls within 6 to 8 days, it is believed that this system presents a candidate compound with the maximum challenge. In order to check factors such as changes in the infectivity of *Plasmodium berghei* or in the susceptibility of the host or to detect technical errors, a group of infected animals treated with pyrimethamine at dose levels producing definite increases in survival time is included as a positive control in every experiment.

In each experiment test compounds are administered in graded doses. With highly active compounds, increases in dose levels are usually followed by increases in the survival time of the treated mice. However, if an active drug is toxic for the host, its toxicity may become a limiting factor; continued increases in dose levels also increase the toxic effects and may result in the diminution of survival times. Deaths prior to the sixth day, when untreated controls begin to die, are regarded as non-parasitic and become the basis for the interpretation that the drug is toxic. Treated animals are kept under observation for 60 days. Survivors at the end of this period of time are considered as cured.

An increase of 100% in mean survival time is considered the minimum effective response for a candidate compound. In calculating mean survival time, toxic deaths and 60 day survivors are not included.

References

1. Osdene, T. S., Russell, P. B. and Rane, L. 2,4,7-Triamino-6-ortho-substituted Arylpteridines. A New Series of Potent Antimalarial Agents. J. Med. Chem. 10, 431-434, 1967.

Methemoglobin formation is induced by primaquine and its analogs. This can be a problem as discussed by R. M. Pinder, "Malaria. The Design, Use and Mode of Action of Chemotherapeutic Agents," 1973, Bristol: Scientechnica (Publishers) LTD; Williams and Wilkins Co., Baltimore, pp 103-105, 118-121.

Antimalarial Activity Test Data

The antimalarial activity data acquired by the two test procedures described above are listed in Tables 2 to 5.

Referring to Table 2, Compound IX as the succinate amine salt (X) was 12.8 times more potent on a molar basis than primaquine diphosphate when calculated by regression analysis and approximately two times more potent than 8-[(4-amino-1-methylbutyl)amino]-6-methoxy-4-methyl-5-(3-trifluoromethylphenoxy)quinoline succinate (Comparative Compound) which is unsubstituted in the 2-position as a radical curative drug against *P. cynomolgi* in the Rhesus monkey.

TABLE 2

Comparison of the Radical Curative Antimalarial Activity of Compound X, the Comparative Compound and Primaquine against *P. cynomolgi* in the Rhesus Monkey

| Compound | Cures Dose (mg/kg × 7) of Salt | | | | | Molar Primaquine Index by Regression Analysis[a] |
|---|---|---|---|---|---|---|
| | 1.3 | 1.0 | 0.316 | 0.10 | 0.0316 | |
| Primaquine diphosphate | 6/6 | 1/2 | 0/2 | 0/2 | — | 1.0 |
| Comparative Compound Succinate | — | 2/2 | 2/2 | 0/2 | 0/2 | 6.8 |
| Compound X (succinate salt) | — | 2/2 | 4/4 | 2/4 | 0/2 | 12.8 |

[a]Ratio of the molar $ED_{50}$ of primaquine, the Comparative Compound and Compound X divided by the $ED_{50}$ of primaquine, respectively.

Referring to Table 3, Compound X had much greater blood schizonticidal activity than primaquine and slightly better activity than the Comparative Compound against trophozoite-induced infections of the Chesson strain of *P. vivax* in the Aotus monkey (Table 3).

TABLE 3

Comparison of the Antimalarial Activity of Primaquine, the Comparative Compound and Compound X against Infections of the Chesson Strain of *P. vivax* in the Aotus Monkey

| Compound | Cures Dose (mg/kg × 3) of Base | | | | | | | |
|---|---|---|---|---|---|---|---|---|
| | 32 | 26 | 16 | 13.3 | 4 | 3.3 | 2 | 1 |
| Primaquine, diphosphate | — | 5/6 | — | 3/8 | — | 0/10 | — | — |
| Comparative Compound Succinate | — | — | 3/3 | — | 4/4 | — | 5/5 | 1/3 |
| Compound X Succinate | 1/1 | — | 3/3 | — | 4/4 | — | — | 2/2 |

Referring to Table 4, Compound X had blood schizonticidal activity in the mouse similar to the Comparative Compound, whereas primaquine diphosphate and 4-methylprimaquine diphosphate were active only at the very high dose level of 160 mg/kg. Further primaquine diphosphate is not curative even at the highest dose of 640 mg/kg and all of the 4-methyl compounds were less toxic than primaquine.

TABLE 4

Comparison of the Antimalarial Activity of Primaquine, 4-Methyl Primaquine, Comparative Compound and Compound X against *P. berghei* in the Mouse

| Compound | Suppressive Activity Dose, mg/kg; ΔMST, Days; 5 Mice | | | | | | | |
|---|---|---|---|---|---|---|---|---|
| | 5 | 10 | 20 | 40 | 80 | 160 | 320 | 640 |
| Primaquine diphosphate | — | — | — | I | I | 9(A) | 2/5T | 5T |
| 4-methyl primaquine diphosphate | — | — | — | I | I | 9(A) | 10(A) | 3C,1T |
| Comparative Compound Succinate | 6 | 4 | [10(A),1C] | 4C | 5C | 5C | 5C | 1T,4C |
| Compound X succinate | 4 | 6 | [9(A),3C,] | 5C | 5C | 5C | 3C | 1T |

I - inactive;
A - Active, ΔMST = increase in survival time in days relative to controls;
T - Toxic death;
C - Cure.

Referring to Table 5, Compound X showed prophylactic activity against sporozoite-induced *P. berghei yoelli* in the mouse; however this activity was slightly less than that observed with the Comparative Compound (Table 5).

TABLE 5

Causal Prophylactic Activity of Comparative Compound and Compound X against Sporozoite Induced *P. berghei yoelli* in the Mouse

| Compound | Cures Dose (mg/kg) (Subcutaneous) of Salt | | | |
|---|---|---|---|---|
| | 2.5 | 10 | 40 | 160 |
| Comparative Compound succinate | 6/15 | 8/20 | 13/15 | 5/5 |
| Compound X succinate | 0/5 | 4/10 | 9/10 | 5/5 |

Referring to Table 6, a comparison of acute toxic of Compound X, the Comparative Compound and primaquine diphosphate in the rat demonstrated that Compound X was less toxic than primaquine or the Comparative Compound when administered either orally or intraperitoneally (Table 6).

TABLE 6

Acute toxicity of Primaquine, Comparative Compound and Compound X in the Rat by Oral or Intraperitoneal Administration

| Species | Sex | Route of Administration | Compound | $LD_{50}$ mg/kg (Salt) (95% Confidence Limit) |
|---|---|---|---|---|
| Rat | Male | Oral | Primaquine | 177 (135–232) |
| Rat | Male | Oral | Comparative Compound | 259 (128–389) |
| Rat | Male | Oral | Compound X | 429 (320–515) |
| Rat | Female | Oral | Primaquine | 244 (193–260) |
| Rat | Female | Oral | Comparative Compound | 401 (368–447) |
| Rat | Female | Oral | Compound X | 416 (376–449) |
| Rat | Male | I.P. | Comparative Compound | 86 (65–109) |
| Rat | Male | I.P. | Compound X | 102 (25–164) |
| Rat | Female | I.P. | Comparative Compound | 54 (42–71) |
| Rat | Female | I.P. | Compound X | 71 (14–114) |

Finally, the data of Table 7 relating to methemoglobin formation are of great importance. Thus, a comparison of the methemoglobin-forming properties of primaquine diphosphate, the Comparative Compound succinate and Compound X succinate in the dog showed that Compound X was a much less potent methemoglobin-forming compound than the Comparative Compound.

TABLE 7

Methemoglobin Formation Caused by Primaquine, Comparative Compound and Compound X in the Dog[a]

| Drug Treatment Group | n[b] | Peak % MHB[c] | Time of Peak[c] MHb (Days) | Slope of[c] MHb Formation | MHb Disappearance[d] Half-Time (Days) | MHb Production[c,e] as AUC Corrected for Baseline |
|---|---|---|---|---|---|---|
| Primaquine[g] | 6 | 6.27 ± 3.86 | 3.92 ± 0.34 | 0.93 ± 0.61 | 7.89 ± 3.30 | 2,138 ± 1,484 |
| Comparative Compound | 3 | 25.3 ± 8.30 | 9.00 ± 1.73 | 0.55 ± 0.28 | 9.14 ± 2.42 | 14,566 ± 5,475 |
| Compound X | 3 | 16.0 ± 7.72 | 6.83 ± 0.72 | 0.61 ± 0.10 | 12.03 ± 9.85[h] | 7,887 ± 3,609 |

[a]Primaquine, Comparative Compound, or Compound X, were administered orally by capsule for four days on days 0, 1, 2 and 3 at a dose of 3 mg/kg primaquine base per day or the molar equivalent. Methemoglobin levels were measured for 30 days.
[b]n = number of dogs
[c]One way analysis of variance indicated significant (p <.05) differences in the means.
[d]One way analysis of variance indicated no difference (p <.05) in the means.
[e]Total methemoglobin production expressed as mg of MHb/ml of blood/hr for a total of 2 days after administration of the first dose.
[f]Area under the % methemoglobin versus time curve (AUC).
[g]Data in this table is composite of data from two experiments performed on the same protocol.
[h]The data of this group was (5.08, 7.71 and 23.30). The long $t_{\frac{1}{2}}$ of one dog constituted the high average and large S.D.

Comparison of equimolar doses of both compounds in the dog demonstrated that, as shown in Table 7, Compound X caused peak levels of methemoglobin of but 16%, whereas with the Comparative Compound the peak level reached 25%, an increase of 56%. Further, total methemoglobin formation, measured as the area under the curve, was 46% less for Compound X than for the Comparative Compound. Thus, the data show clearly that Compound X is significantly less toxic in terms of methemoglobinemia and that the drug will be considerably safer to administer to animals and humans.

Further, the high antimalarial activity of Compound X was completely unexpected. Examples of analogs of Compound X bearing substituents other than methoxy in the 2-position are shown in Table 8. All four analogs are completely inactive against *P. berghei* in the mouse. Thus it would not be expected even to someone skilled in the art that Compound X would be curative when the 2-chloro, 2-hydroxy, 2-(4-chlorophenoxy) and the 2-(4-benzyloxy) analogs are devoid of or poorly curative of antimalarial activity.

TABLE 8

2-Substituted Analogs of compound X

[Structure of compound: quinoline with CH₃O group, O-phenyl-CF₃ group, CH₃·Succinate, R₅ substituent, and HNCH(CH₃)(CH₂)₃NH₂ group]

| | | Rane, *P. berghei*, 5 mice, mg/kg | | | | | | P. cynomolgi, mg/kg (×7), Seato | | | |
|---|---|---|---|---|---|---|---|---|---|---|---|
| | R₅ | 20 | 40 | 80 | 160 | 320 | 640 | 1.0 | 0.316 | 0.1 | 0.0316 |
| Compound X | OCH₃ | A | 3C 5C | 5C | 5C | 3C | 1T | 2/2C | 4/4C | 2/4C | 0/2C |
| Analog 1 | OH | Inactive and non-toxic | | | | | | No Data | | | |
| Analog 2 | —O—⟨phenyl⟩—Cl | Inactive and non-toxic | | | | | | No Data | | | |
| Analog 3 | —OCH₂—⟨phenyl⟩—Cl | Inactive and non-toxic | | | | | | No Data | | | |
| Analog 4 | Cl | I | 1C | 4T | 1T | | | 2/2C | 1/2C | 0/1C | |

Reactions in the Preparation of 8-(4-amino-1-methylbutylamino)-2,6-dimethoxy-4-methyl-5-(3-trifluoromethylphenoxy) quinoline (IX) and succinate salt (X)

The starting compound was 8-amino-6-methoxy-4-methyl-5-(3-trifluoromethylphenoxy)quinoline (I), the preparation of which is described in detail in U.S. Pat. No. 4,431,807. The reaction sequence in preparing Compound X was as follows:

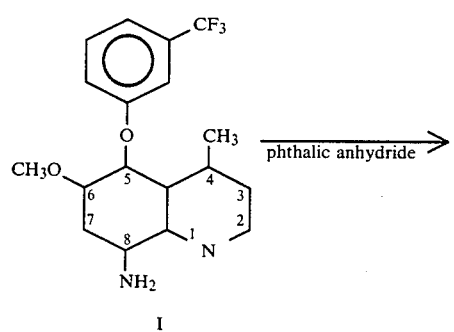
I
phthalic anhydride →
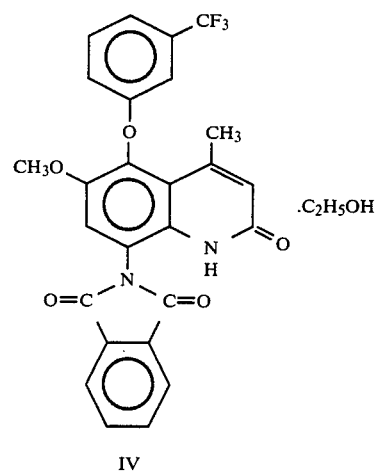
IV
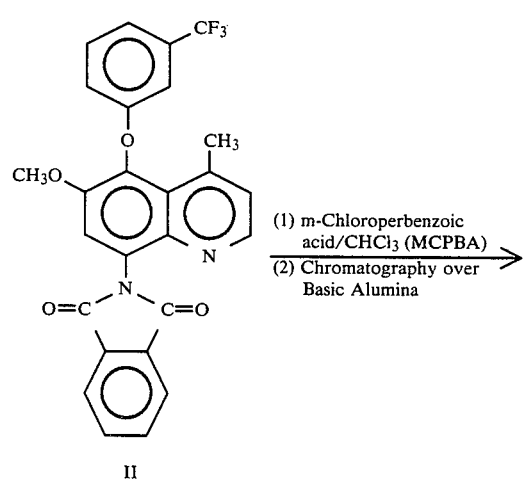
II
(1) m-Chloroperbenzoic acid/CHCl₃ (MCPBA)
(2) Chromatography over Basic Alumina →
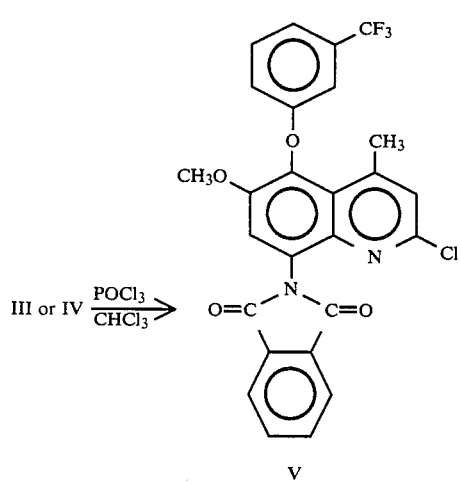
III or IV $\xrightarrow{POCl_3/CHCl_3}$
V
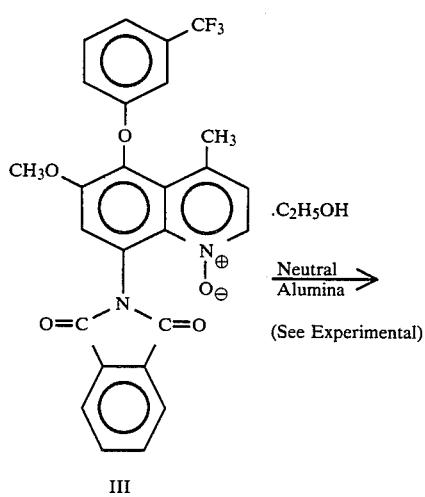
III
Neutral Alumina → (See Experimental)
V $\xrightarrow{H_2NNH_2/EtOH}$
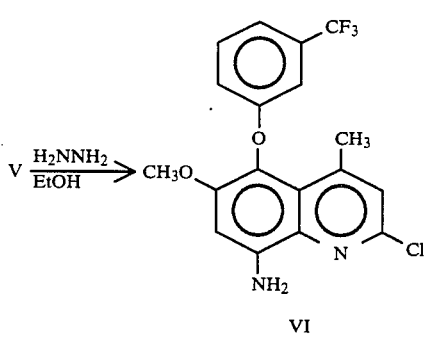
VI
VI + $\xrightarrow{NaH/MeOH/DMF}$
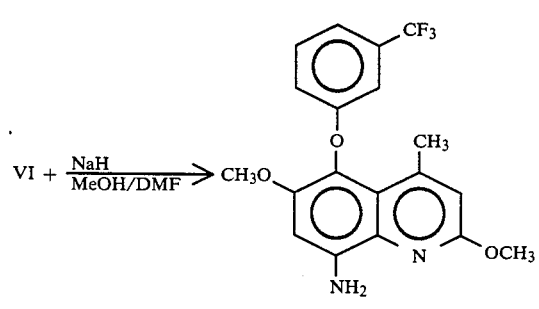
VII

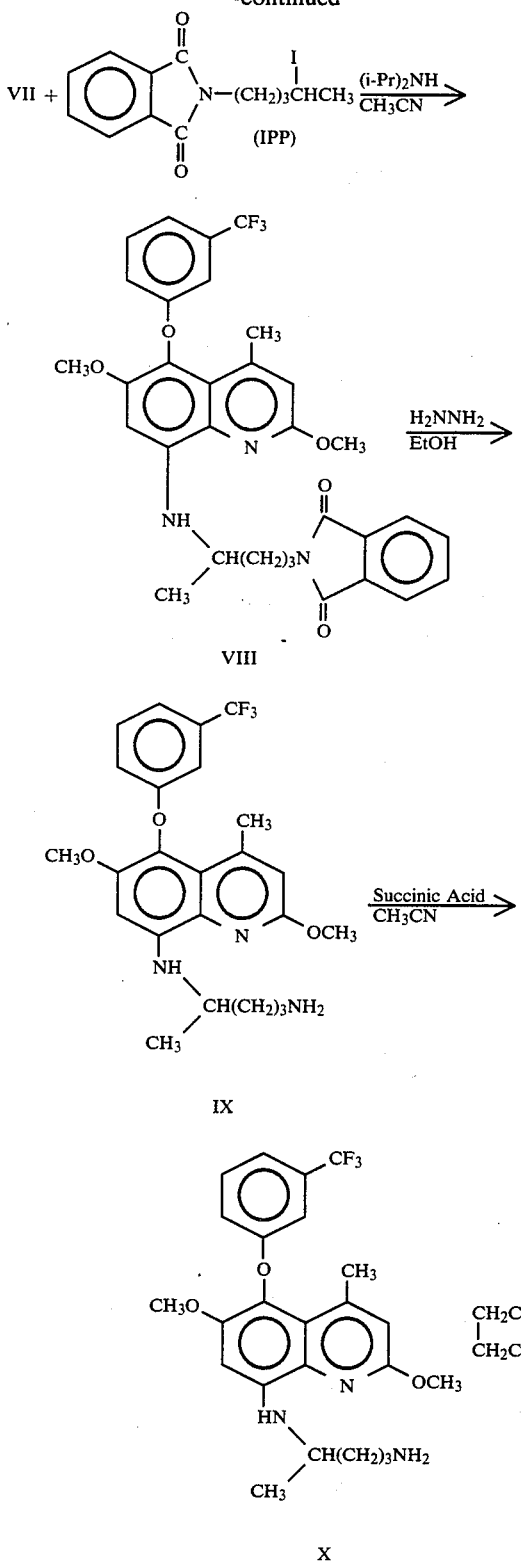

1-oxide III. Intermediate III was treated directly (preferred procedure) with phosphorus oxychloride to afford the 2-chloro derivative V. However, it was discovered also that treatment of the reaction mixture from the oxidation step with a combination of basic and neutral alumina gave the 2-quinolone IV which was converted also with phosphorus oxychloride to give the 2-chloro derivative V, albeit in lower yield.

In the next step, the 2-chloro intermediate V was treated with hydrazine by a standard procedure to remove the 8-phthalimido protecting group (see U.S. Pat. No. 4,431,807) to give 8-amino-2-chloroquinoline VI. The latter compound is a very versatile intermediate to introduce various alkoxy and aryloxy groups into the 2-position of the molecule such as the methoxy, ethoxy, 4-phenoxy and 4-chlorobenzyl, for example.

Thus, the 8-amino-2-chloroquinoline VI was allowed to react with a solution of sodium methylate in DMF (prepared under nitrogen by adding sodium hydride to a solution of methanol in DMF accompanied by the liberation of hydrogen). This procedure afforded 8-amino-2-methoxyquinoline VII. The introduction of the 8-(4-amino-1-methylbutyl) side chain was accomplished in the same manner as for the COMPARATIVE COMPOUND (U.S. Pat. No. 4,431,801). Thus intermediate VII was treated with 4-iodo-1-phthalimidopentane to give the target precursor 8-(4-phthalimido-1-methylbutylamino)quinoline VIII. The phthalimido group was removed with hydrazine to give the title compound free base IX. The free base was treated with succinic acid in a suitable solvent system to give the 2-methoxy target compound X as the succinic acid salt.

As stated, these same procedures can be used for the preparation of compounds with various 5-unsubstituted and 5-substituted phenyl groups and various 8-alkylene amino groups as shown in U.S. Pat. No. 4,431,807. Based upon the studies with the compounds of U.S. Pat. No. 4,431,807 all would be predicted to be active in the same manner as X.

SPECIFIC DESCRIPTION

Preparation of 8-(4-Amino-1-methylbutylamino)-2, 6-dimethoxy-4-methyl-5-(3-trifluoromethylphenoxy)-quinoline Succinate (X).

6-Methoxy-4-methyl-8-phthalimido-5-(3-trifluoromethylphenoxy)quinoline (II): A mixture of 8-amino-6-methoxy-4-methyl-5-(3-trifluoromethylphenoxy)quinoline (I) (6.96 g, 20 mmol) and phthalic anhydride (3.25 g, 22 mmol) in xylene (100 mL) was refluxed with water removal via a Dean-Stark trap for 24 hours. After cooling, filtration gave 9.5 g (100%) of the title compound, mp 228°–30° C. Recrystallization from ethanol raised the mp to 228°–31° C.

Anal. Calcd for $C_{26}H_{17}N_2F_3O_4$: C, 65.27; H, 3.58; N, 5.86; F, 11.91. Found: C, 65.12; H, 3.63; N, 5.92; F, 11.67.

6-Methoxy-4-methyl-8-phthalimido-5-(3-trifluoromethylphenoxy)-quinoline-1-oxide Ethanolate (III): Following the general procedure of Craig and Purushothaman (J. Org. Chem. 35, 1721 (1970)), the preceding compound (2.39 g, 5 mmol) and 100% m-chloroperbenzoic acid (0.86g, 5 mmol) in chloroform (CHCl3, (15 mL) gave, after chromatography (basic alumina, 2% MeOH in CHCl3) and recrystallization from ethanol, 1.16 g (43%) of the title compound as the ethanolate, mp 215°–218° C. Further recrystallization from ethanol did not change the melting point.

Anal. Calcd for $C_{26}H_{17}N_2F_3O_5 \cdot C_2H_6O$: C, 62.22; H, 4.29; N, 5.18; F, 10.54. Found: C, 62.11; H, 4.44; N, 4.86; F, 10.42.

6-Methoxy-4-methyl-8-phthalimido-5-(3-trifluoromethylphenoxy)quinoline-2-one Ethanolate IV: One preparation of 6-methoxy-4-methyl-8-phthalimido-5-(3-trifluoromethylphenoxy)quinoline-1-oxide ethanolate was carried out on a larger scale, as previously described. The concentrated reaction mixture was put on a column of alumina [prepared by packing Baker basic alumina (500g) on top of Baker neutral alumina (400g)]. Elution with chloroform-methanol (98:2) gave, after evaporation, a 10 yellow solid. Recrystallization from EtOH gave the title compound, 18 g, (51%), mp 199.5°–201.5° C. Recrystallization from ethyl acetate gave material with mp 199°–201° C.

Anal. Calcd for $C_{26}H_{17}N_2F_3O_5 \cdot C_2H_6O$: C, 62.22; H, 4.29; N, 5.18; F, 10.54. Found: C, 62.28; H, 4.36; N, 5.43; F, 10.65.

2-Chloro-6-methoxy-4-methyl-8-phthalimido-5-(3-trifluoromethylphenoxy)quinoline (V)

(A) From 6-methoxy-4-methyl-8-phthalimido-5-(3-trifluoromethylphenoxy)quinoline-1-oxide Ethanolate (III): A solution of 6-methoxy-4-methyl-8-phthalimido-5-(3-trifluoromethylphenoxy)quinoline-1-oxide ethanolate (32.7g, 60.5 mmol) in CHCl$_3$ (500 mL) was treated with POCl$_3$ (55 mL, 92 g, 602 mmol) over 15 min. The solution was refluxed 2 hours, cooled, poured onto ice (1500 mL) and the pH was adjusted to 12 with 20% NaOH (700 g). The separated aqueous layer was extracted with CHCl$_3$ (2×200 mL). The extract was washed with H$_2$O (2×200 mL), saturated NaHCO$_3$ (20 mL), dried (MgSO$_4$) and evaporated in vacuo to a white solid. Recrystallization from ethanol gave 23.2 g (75%) of 1st crop title compound, mp 227°–229° C. Further recrystallizations did not change the melting point.

Anal. Calcd for $C_{26}H_{16}N_2ClF_3O_4$: C, 60.89; H, 3.14; N, 5.46; Cl, 6.91; F, 11.11. Found: C, 60.61; H, 2.97; N, 5.24; Cl, 6.94; F, 11.01.

(B) From 6-Methoxy-4-methyl-8-phthalimido-5-(3-trifluoromethylphenoxy)quinoline-2-one Ethanolate (IV): A solution of 6-methoxy-4-methyl-8-phthalimido-5-(3-trifluoromethylphenoxy)quinoline-2-one ethanolate (1 g, 1.85 mmol) in CHCl$_3$ (10 mL) was treated with POCl$_3$ (1.5 mL, 2.5 g, 16.4 mmol) as described above to give, after recrystallization from EtOH, 0.3 g (32%) of title compound, mp 225°–227° C. Further recrystallization from EtOH raised the mp to 227°–229° C. [mixed mp with material prepared in A) 226°–229° C.].

Anal. Calcd for $C_{26}H_{16}N_2ClF_3O_4$: C, 60.89; H, 3.14; N, 5.46; Cl, 6.91; F, 11.11. Found: C, 61.13; H, 3.11; N, 5.47; Cl, 6.90; F, 10.96.

8-Amino-2-chloro-6-methoxy-4-methyl-5-(3-trifluoromethylphenoxy)quinoline (VI): A suspension of 2-chloro-6-methoxy-4-methyl-8-phthalimido-5-(3-trifluoromethylphenoxy)quinoline (23.2 g, 45.2 mmol) in ethanol (900 mL) was treated with excess hydrazine hydrate (75%, 16.75 mL) and the mixture was refluxed with mechanical stirring for 3 hours. After cooling, the solids were collected and washed with CH$_2$Cl$_2$. The combined filtrate and washings were evaporated in vacuo to a small volume and dissolved in CH$_2$Cl$_2$ (500 mL). The solution was extracted with 20% KOH (3×200 mL), and with brine, dried (K$_2$CO$_3$) and evaporated in vacuo to an amber gum. Recrystallization from cyclohexane-ligroin (5:2, 500 mL) with charcoaling gave 15.4 g (89%) of 1st crop title compound, mp 133°–135° C. Further recrystallization did not change the melting point.

Anal. Calcd for $C_{18}H_{14}N_2ClF_3O_2$: C, 56.48; H, 3.69; N, 7.32; Cl, 9.26; F, 14.89. Found: C, 56.35; H, 3.93; N, 7.30, Cl, 9.51; F, 14.74.

8-Amino-2,6-dimethoxy-4-methyl-5-(3-trifluoromethylphenoxy)quinoline (VII): A solution of MeOH (0.824 g, 25.8 mmol) in DMF (anhyd., 60 mL) under a N$_2$ atmosphere was treated with NaH (50% oil dispersion, 1.02 g, 21.4 mmol). After H$_2$ evolution ceased, 8-amino-2-chloro-6-methoxy-4-methyl-5-(3-trifluoromethylphenoxy)quinoline (7.5 g, 19.6 mmol) was added and the mixture was heated at 90° C. for 1 hour. After cooling, the reaction mixture was poured onto ice (600 mL) and extracted with CH$_2$Cl$_2$. The CH$_2$Cl$_2$ was washed with H$_2$O (3X), dried (K$_2$CO$_3$) and evaporated in vacuo. This material was combined with material obtained from two smaller runs (on 0.5 g and 2.0 g of the chloroamine) and chromatographed on silica gel (EM, 500 g) with 1% methanol in CH$_2$Cl$_2$. The yellow (product) band was collected and evaporated in vacuo to give 8.5 g (86%) of the title compound, mp 113°–115° C. Recrystallization from hexanes raised the mp to 114°–117° C.

Anal. Calcd for $C_{19}H_{17}N_2F_3O_3$: C, 60.32; H, 4.53; N, 7.40; F, 15.06. Found: C, 60.50; H, 4.69; N, 7.36; F, 15.33.

2,6-Dimethoxy-4-methyl-8-(4-phthalimido-1-methylbutylamino)-5-(3-trifluoromethylphenoxy)quinoline (VIII): A mixture of 8-amino-2,6-dimethoxy-4-methyl-5-(3-trifluoromethylphenoxy)quinoline (8.0 g, 21.2 mmol), diisopropylamine (2.14 g, 21.2 mmol) and 4-iodo-1-phthalimidopentane (IPP) (7.26 g, 21.2 mmol) in CH$_3$CN (40 mL) was refluxed for 24 hours after which time additional diisopropylamine (2.14 g, 21.2 mmol) and IPP (7.26 g, 21.2 mmol) were added. After refluxing a further 24 hours, more diisopropylamine (1.07 g, 10.6 mmol) and IPP (3.63 g, 10.6 mmol) were added and refluxing was continued a further 24 hours. The cooled mixture was diluted with H$_2$O (20 mL) and stirred in an ice bath until crystallization was complete. Filtration and recrystallization from IPA gave 8.4 g (67%) of 1st crop title compound, mp 120°–124° C. Further recrystallization raised the mp to 121°–124° C.

Anal. Calcd for $C_{32}H_{30}N_3F_3O_5$: C, 64.75; H, 5.09; N, 7.08; F, 9.60. Found: C, 64.58; H, 4.79; N, 7.06; F, 9.85.

8-(4-Amino-1-methylbutylamino)-2,6-dimethoxy-4-methyl-5-(3-trifluoromethylphenoxy)quinoline Succinate (X): A solution of the preceding compound (7.5 g, 12.6 mmol) in ethanol (500 mL) was treated with excess hydrazine hydrate (75%, 4.5 mL) and refluxed for 10 hours. After cooling overnight, the solids were collected and washed with CH$_2$Cl$_2$. The combined filtrate and washings were evaporated in vacuo to a small volume and diluted with CH$_2$Cl$_2$ (200 mL). The CH$_2$Cl$_2$ solution was washed with 20% KOH (3×75 mL), brine, dried (K$_2$CO$_3$) and evaporated in vacuo to give the free base IX as an oil. This oil was dissolved in CH$_3$CN (20 mL) and treated with a solution of succinic acid (1.42 g, 12 mmol) in a mixture of MeOH (5 mL) and CH$_3$CN (20 mL) to give 6.3 g (86%) of title succinate salt X. Recrystallization from CH$_3$CN gave 5.7 g (78%) of 1st crop title compound, mp 146°–149° C. Further recrystallization did not raise the melting point.

Anal. Calcd for $C_{24}H_{28}N_3F_3O_3 \cdot C_4H_6O_4$: C, 57.82; H, 5.89; N, 7.23; F, 9.80. Found: C, 57.86; H, 6.04; N, 7.36; F, 10.02.

It is intended only that the foregoing description be illustrative of the present invention and that the invention be limited only by the hereinafter appended claims

We claim:

1. A compound of the formula:

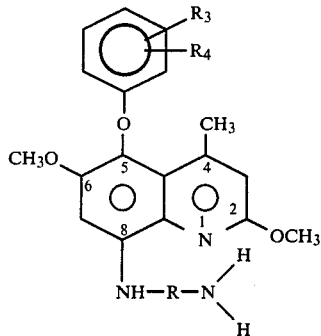

wherein R is an alkylene group which is

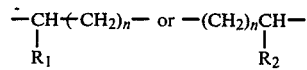

wherein n is 3 or 4, wherein $R_1$ and $R_2$ are methyl or ethyl, wherein $R_3$ and $R_4$ are hydrogen, chloro, bromo, fluoro, trifluoromethyl or methoxy groups and wherein the compound is a free amine or a pharmaceutically acceptable acid amine salt.

2. The compound of claim 1 wherein R is

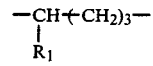

and wherein $R_1$ is methyl.

3. The compound of claim 1 wherein $R_3$ is trifluoromethyl and $R_4$ is hydrogen.

4. The compound of claim 1 as the succinate amine salt.

5. The compound of claim 1 which is 8-(4-amino-1-methylbutylamino)-2,6-dimethoxy-4-methyl-5-(3-trifluoromethylphenoxy)quinoline as a free amine or a pharmaceutically acceptable acid amine salt.

* * * * *